United States Patent [19]
Ohike et al.

[11] Patent Number: 5,691,538
[45] Date of Patent: Nov. 25, 1997

[54] TWIN-DETECTOR TYPE SCINTILLATION CAMERA APPARATUS CAPABLE OF SETTING DETECTING DIRECTIONS OF DETECTORS IN DESIRED DIRECTION

[75] Inventors: Masahito Ohike, Noda; Minoru Inamoto, Kashiwa, both of Japan

[73] Assignee: Hitachi Medical Corporation, Tokyo, Japan

[21] Appl. No.: 668,267

[22] Filed: Jun. 20, 1996

[30] Foreign Application Priority Data

Jun. 23, 1995 [JP] Japan .................................. 7-179693

[51] Int. Cl.⁶ ...................................................... G01T 1/166
[52] U.S. Cl. ................................ 250/363.05; 250/363.04
[58] Field of Search .......................... 250/363.05, 363.04

[56] References Cited

U.S. PATENT DOCUMENTS

| 4,651,007 | 3/1987 | Perusek et al. | 250/363.04 |
| 5,534,701 | 7/1996 | Pierfitte et al. | 250/363.04 |

FOREIGN PATENT DOCUMENTS

| 0532152 | 3/1993 | European Pat. Off. | 250/363.05 |
| 58-30685 | 2/1983 | Japan | 250/363.04 |
| 61-83984 | 4/1986 | Japan | 250/363.04 |
| 4-256885 | 9/1992 | Japan | 250/363.04 |

*Primary Examiner*—Constatine Hannaher
*Attorney, Agent, or Firm*—Antonelli, Terry, Stout, & Krauss, LLP

[57] ABSTRACT

A twin-detector type scintillation camera apparatus includes a pair of detectors which is disposed in opposition to each other with a table for supporting an object under examination being interposed therebetween to detect radioactive rays emitted from the object, a rotatable frame disposed in a plane extending in a direction orthogonal to a longitudinal axis of the table and supports the paired detectors at one side thereof, a translation mechanism capable of moving the paired detectors in parallel with each other in a plane extending orthogonally to the longitudinal axis of the object supporting table while maintaining parallelism between the paired detectors, an approaching mechanism which is capable of moving the pair of detectors in directions orthogonal to the directions in which the detectors are moved in parallel with each other, and a rotating mechanism capable of driving rotationally each of the detectors by a predetermined angular distance from a given position.

5 Claims, 6 Drawing Sheets

TWIN-DETECTOR TYPE SCINTILLATION CAMERA APPARATUS CAPABLE OF SETTING DETECTING DIRECTIONS OF DETECTORS IN DESIRED DIRECTION

BACKGROUND OF THE INVENTION

The present invention relates generally to a dual- or twin-detector type scintillation camera apparatus which includes a pair of detectors disposed in opposition to each other with an object under test or examination being interposed therebetween and which can be employed for conducting diagnosis based on nuclear-medical images. More specifically, the invention is concerned with a twin-detector type scintillation camera apparatus which is capable of reducing a time taken for acquiring image data while ensuring improvement of image quality of pictures obtained in single photon emission computer tomography (hereinafter referred to as SPECT in abbreviation) for diagnosing or examining the heart of a human being.

For having better understanding of the present invention, technical background thereof will first be described in some detail. FIG. 7 is a view showing a conventional twin-detector type scintillation camera apparatus known heretofore. As can be seen in the figure, the conventional scintillation camera apparatus is comprised of a pair of detectors 3a and 3b disposed in opposition to each other with an object supporting table 1 being interposed therebetween employed for detecting radioactive rays emitted from an object 2 under examination lying on the object supporting table 1, a rotatable frame 4 disposed in a plane extending orthogonally to the longitudinal direction of the object supporting table 1 and supporting the pair of detectors 3a and 3b at one side, wherein the image data originating in the object 2 under examination is acquired by means of the detectors 3a and 3b while revolving them around the longitudinal axis of the object supporting table 1. At this juncture, it should be added that the rotatable frame 4 is supported in an upstanding or erect state internally of a detector frame or stand 5.

In the conventional twin-detector type scintillation camera apparatus described above, the pair of detectors 3a and 3b are disposed above and beneath the object supporting table 1, respectively, in opposition to each other and fixedly mounted in such disposition that a relative angle formed between the detectors 3a and 3b always remains constant at zero degree. The twin-detector type scintillation camera apparatus mentioned above is advantageous over a single-detector type scintillation camera apparatus also known heretofore in that the data for the SPECT image over a whole circumference of the object 2 under examination can be acquired by revolving each of the detectors 3a and 3b only by a half of a complete rotation, as can be seen from FIG. 8. Besides, when taking a picture of an object 2 under examination over the whole body thereof inclusive of rear- and frontsides thereof along the longitudinal axis of the object 2 under examination, it is sufficient to move each of the detectors 3a and 3b only by a single pass without need for moving the detectors reciprocatively, as illustrated in FIG. 7. In this way, the time required for acquiring or collecting the image data can be reduced by a half when compared with the single-detector type scintillation camera apparatus, which in turn means that the effectiveness of diagnosis can be enhanced correspondingly.

However, in the case of acquiring the image data for the SPECT image of the heart among others, it is sufficient to collect the image data only over an angular range of 180 degrees around the object 2 under examination because the heart 6 is offset to one side of the object under examination as viewed in a cross-section thereof, as can be seen from FIG. 9. Nevertheless, because the pair of detectors 3a and 3b are fixed at the relative angle equal to zero in the conventional scintillation camera apparatus, as mentioned previously, the image data necessary for the diagnosis can be acquired effectively only with the aid of the second detector 3b in the diagnosis illustrated in FIG. 9, whereas the image data collected by the second detector 3a are of no use. In other words, in the case of the tomographic diagnosis of the heart, the advantage provided by the twin-detector type scintillation camera apparatus as mentioned previously can not be enjoyed at all. More specifically, the time taken for acquiring the image data by using the twin-detector type scintillation camera apparatus for the examination or diagnosis of the heart is utterly same as that required for when the single-detector type scintillation camera apparatus is used. In other words, the advantage that the time taken for acquiring the image data an be reduced with the twin-detector type scintillation camera apparatus can no more be ensured for the diagnosis of the heart.

Certainly, a twin-detector type scintillation camera apparatuses in which the angle formed by a pair of detectors is variable have already been proposed, as disclosed in the specifications of U.S. Pat. No. 5,444,252 and JP-A-6-82557 whose priority document is U.S. patent application Ser. No.07/704,759. In these twin-detector type scintillation camera apparatuses, the detectors are so arranged as to be driven along respective circular paths independent of each other with both of the detectors being movable in the radial direction as well.

However, when the angle formed by the pair of detectors is selectively set at e.g. 90 degrees in the twin-detector type scintillation camera apparatus proposed in JP-A-6-82557 for taking a SPECT image of the heart in the manner as illustrated in FIG. 9, it is certainly possible to collect the image data over a range of 180 degrees around the object 2 under examination by rotating each of the detectors for an angular distance of 90 degrees. It is however impossible to move the pair of detectors within a plane extending orthogonally to the longitudinal direction of the object supporting table (i.e., the translation of the detectors) or move the paired detectors closely toward the table at given positions of the detectors orthogonally to the direction of the translation or rotate the detectors on their axes, respectively, at the respective positions in succession to the movements mentioned above. To say in another way, it is impossible to set the pair of detectors arbitrarily at any desired angle relative to the object under examination lying on the supporting table or set the sensing directions of the detectors in any desired direction for the purpose of avoiding so-called dead zones for the acquisition of the image data. Thus, it is safe to say that the conventional twin-detector type scintillation camera apparatuses suffer a problem that difficulty is encountered in obtaining tomographic image of a satisfactory quality within a reasonably short time.

SUMMARY OF THE INVENTION

In the light of the state of the art described above, it is an object of the present invention to provide a twin-detector type scintillation camera apparatus which can collect or make available SPECT image data particularly in taking tomography of the heart within a shortened time with a improved or enhanced image quality to thereby overcome or mitigate the problem of the conventional scintillation camera apparatuses described above.

In view of the above and other objects which will become apparent as the description proceeds, there is provided

3 according to a general aspect of the present invention a twin-detector type scintillation camera apparatus which includes a pair of detectors disposed in opposition to each other with a table for supporting an object under examination being interposed therebetween for detecting radioactive rays emitted from the object and a rotatable frame disposed in a plane extending in a direction orthogonal to a longitudinal axis of the table and for supporting the paired detectors rotatably about the respective axes at one side at the frame for acquiring image data originating in the object under examination while rotating the detectors about the longitudinal axis of the object supporting table, wherein the pair of detectors are so supported as to be movable in parallel to each other in a plane extending orthogonally to the longitudinal axis of the object supporting table while being moved in the directions approaching the object supporting table, and wherein the detectors are rotatable around respective supporting axes at given positions thereof.

Further, the supporting mechanism for supporting the pair of detectors on the rotatable frame includes a translation mechanism mounted at one side of the rotatable frame for moving the pair of the detectors in parallel with each other, while being interlocked, in the plane extending orthogonally to the longitudinal axis of the object supporting table, approaching mechanisms installed at the translation mechanism for moving, respectively, the pair of detectors in directions orthogonal to the direction in which the detectors are moved in parallel with each other by the translation mechanism, and rotating mechanisms provided in association with the approaching mechanisms, respectively, for rotating the detectors on or about the axes thereof, respectively, in the plane extending orthogonally to the longitudinal direction mentioned above.

By driving selectively and arbitrarily the translation mechanism, approaching mechanism and the rotating mechanism, the pair of detectors supported on the rotatable frame mentioned above can be set at any given relative angle not greater than 180 degrees, while the front faces of the detectors can be approached as close as possible to the object under examination, wherein the detecting or sensing direction of the individual detectors can be set arbitrarily as desired.

With the arrangement of the twin-detector type scintillation camera apparatus described above, it is possible to avoid the dead zone for the acquisition of image data. Thus, in acquisition of the SPECT image data, in particular, for the heart, the time taken therefor can remarkably be shortened while enhancing the image quality.

The above and other objects, features and attendant advantages of the present invention will more easily be understood by reading the following description of the preferred embodiments thereof taken, only by way of example, in conjunction with the accompanying drawings.

BRIEF DESCRIPTION OF THE DRAWINGS

In the course of the description which follows, reference is made to the drawings, in which.

4

Figure 5:
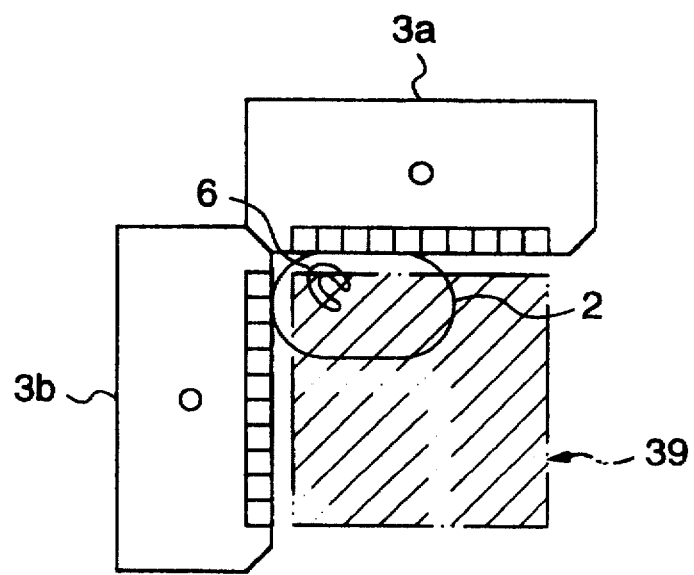
Figure 6:
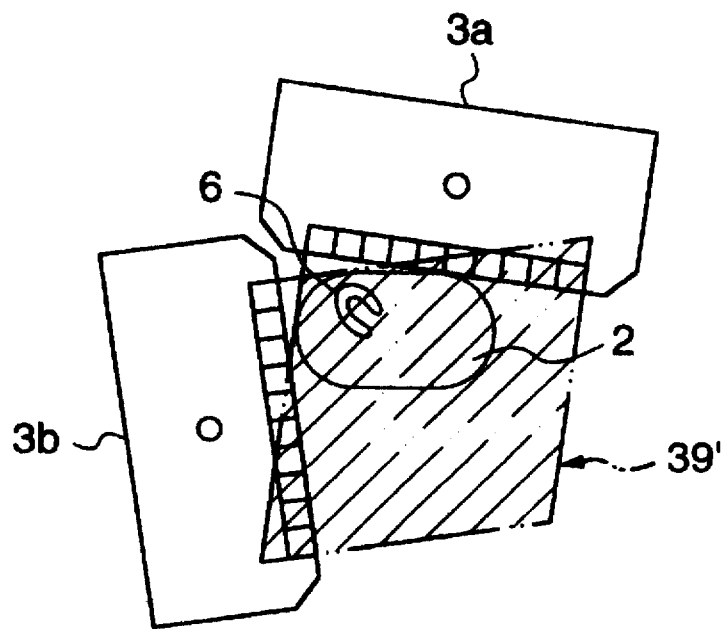
Figure 7:
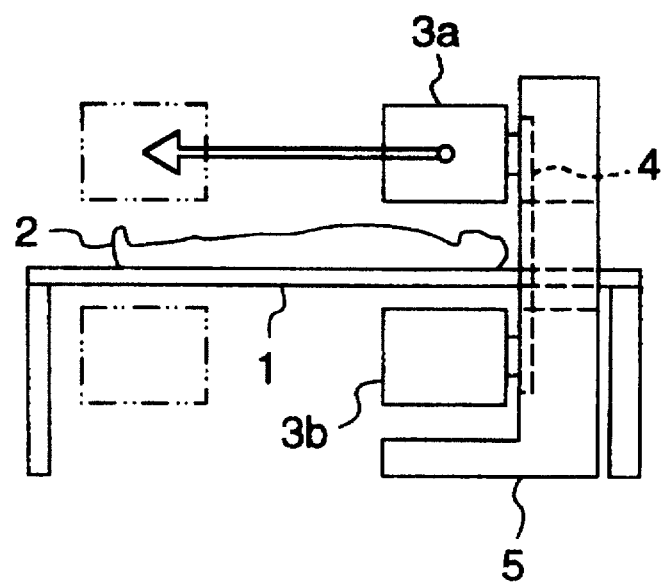
Figure 8:
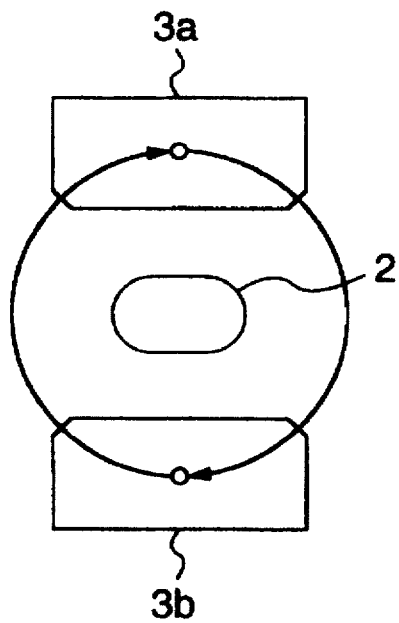
Figure 9:
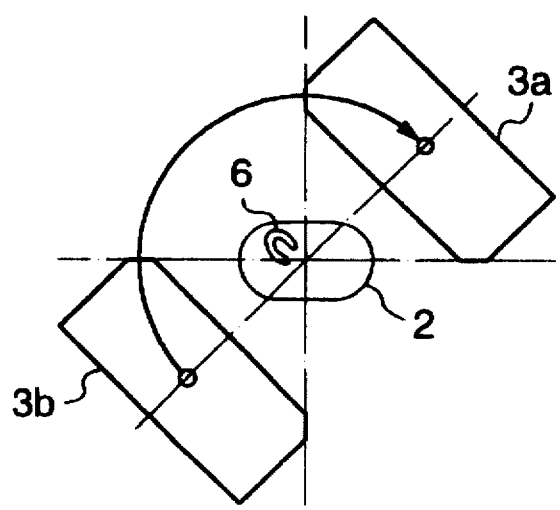

FIG. 5 is a view illustrating a state where the detectors are moved so closely to an object under examination that the front faces thereof are put into contact with a peripheral surface of the object;

FIG. 6 is a view illustrating a state where a zone of an effective visual field is varied by rotating the individual detectors;

FIG. 7 is a schematic elevational view showing a conventional twin-detector type scintillation camera apparatus known heretofore;

FIG. 8 is a view for illustrating operation of the conventional apparatus shown in FIG. 7 involved in acquiring SPECT image data over a whole trajectory around an object under examination; and FIG. 9 is a view for illustrating operations of the conventional twin-detector type scintillation camera apparatus in acquiring a cardiac SPECT image of an object under examination.

DESCRIPTION OF THE PREFERRED EMBODIMENTS

Now, the present invention will be described in detail in conjunction with what is presently considered as preferred or typical embodiments thereof by reference to the drawings. In the following description, like reference characters designate like or corresponding parts throughout the several views. Also in the following description, it is to be understood that such terms as "leftward", "rightward", "front", "rear", "top", "bottom", "counterclockwise", "clockwise", and the like are words of convenience and are not to be construed as limiting terms.

Figure 1:
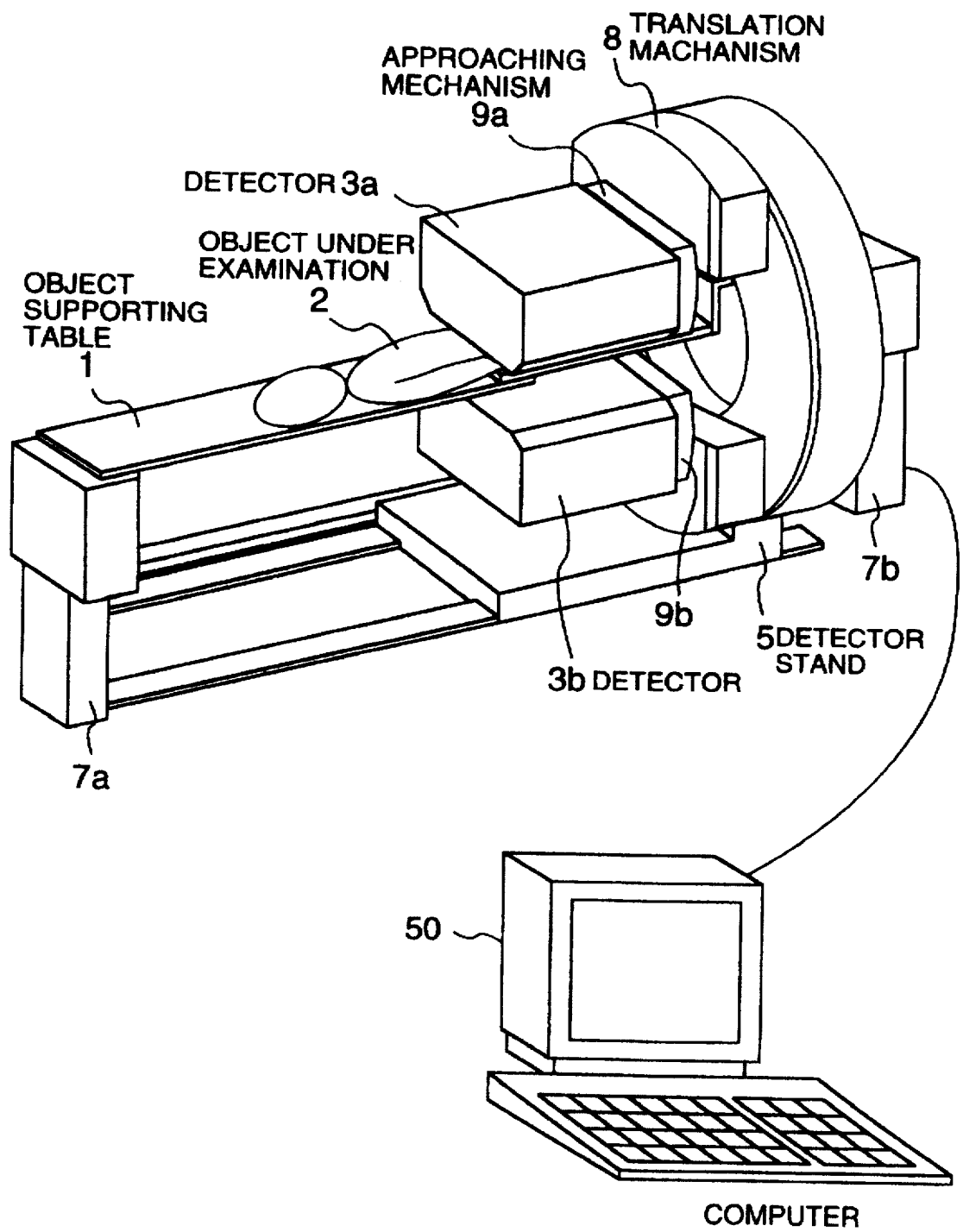
FIG. 1 is a perspective view showing schematically camera system according to an exemplary embodiment of present invention.
Figure 2:
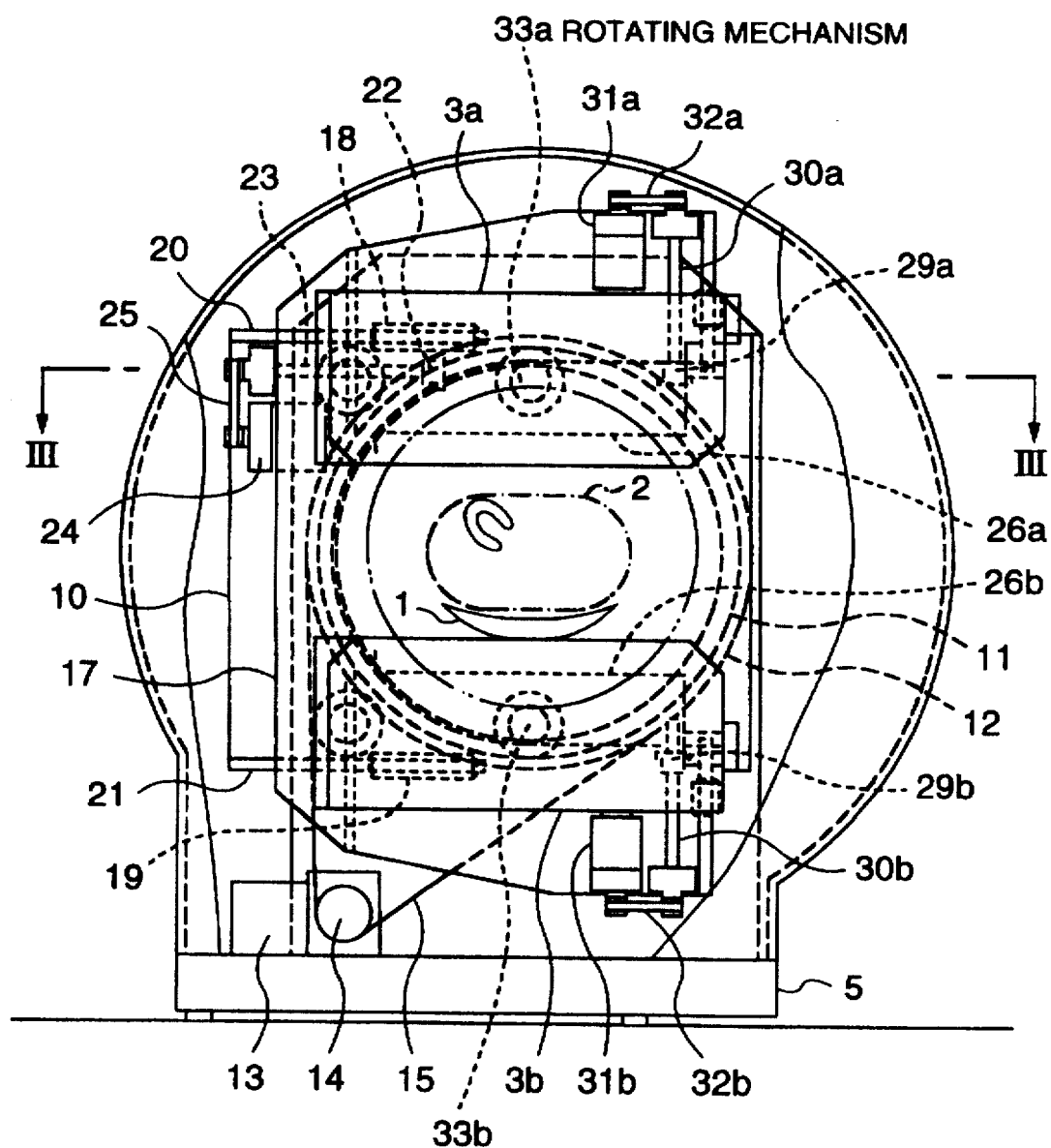
FIG. 2 is an enlarged front side view of the same.
Figure 3:
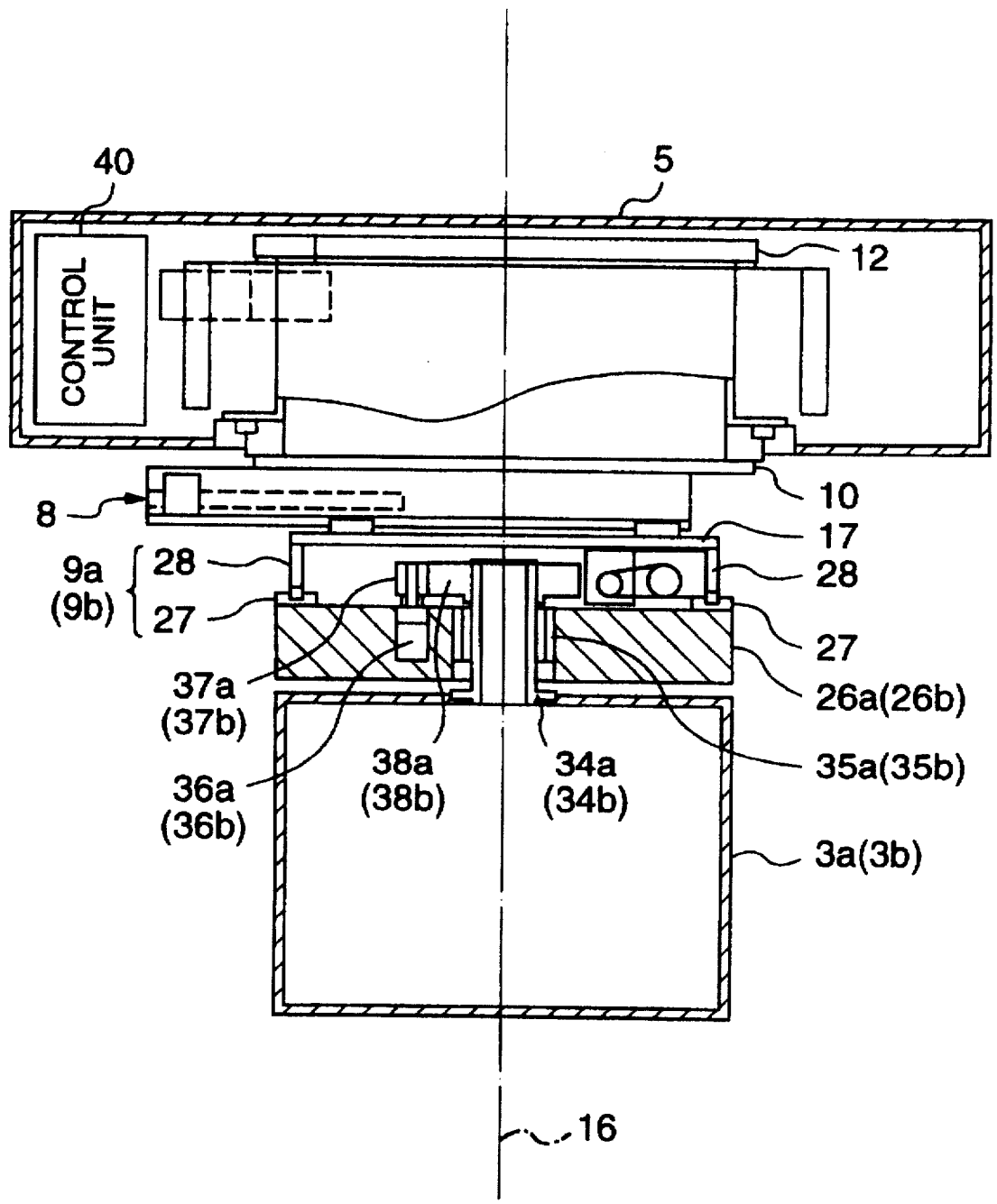
FIG. 3 is a sectional view of the same taken along a line III—III in FIG. 2.

FIG. 1 is a perspective view showing a twin-detector type scintillation camera apparatus according to an exemplary embodiment of the present invention, FIG. 2 is an enlarged front side view of the same, and FIG. 3 is a sectional view thereof taken along a line III—III in FIG. 2. Referring to FIG. 1, the twin-detector type scintillation camera apparatus includes an object supporting table 1 for supporting an object 2 under examination such as a human being under diagnosis in a recumbent or lying state, wherein the object supporting table 1 is supported in a horizontal disposition by means of supporting platforms 7a and 7b disposed at both ends as viewed in the longitudinal direction in FIG. 1, wherein the object supporting table 1 can be adjusted in respect to the height thereof. Disposed above and below the object supporting table 1 are a pair of detectors 3a and 3b, respectively, which face in opposition to each other with the object supporting table 1 being interposed therebetween. The detectors 3a and 3b serve to detect radioactive rays emitted from a radio isotope dosed on the object 2 under examination lying on the object supporting table 1. Two detectors 3a and 3b mentioned above are supported on a rotatable frame supported in an upstanding disposition internally of a detector stand 5 (see FIG. 2). More specifically, the rotatable frame is disposed internally of the detector stand 5 in a plane extending orthogonally to the longitudinal axis of the object supporting table 1, wherein the pair of detectors 3a and 3b are supported at one side of the rotatable frame.

According to the invention incarnated in the illustrated embodiment, the supporting of the two detectors 3a and 3b on the rotatable frame is so realized that these detectors 3a and 3b can move in parallel with each other in a plane extending orthogonally to the longitudinal axis of the object supporting table 1 (also referred to as the translational movement of the detectors) and additionally each of the detectors 3a and 3b can move toward and away from the object supporting table 1 in a direction orthogonal to the direction of the translational movement mentioned above and that each of the detectors 3a and 3b can be rotated, respectively, around the associated supporting axes at given positions relative to the object supporting table 1. Further, in FIG. 1, reference numeral 50 denotes generally a computer with the aid of which operator can input commands for controlling operation of the scintillation camera apparatus and on which an image generated by processing the image data as acquired is displayed.

Next, referring to FIGS. 1 to 3, description will be made in detail of the structures of mechanisms for supporting the two detectors 3a and 3b. First referring to FIG. 1, the whole assembly of the supporting mechanisms for the detectors 3a and 3b is composed of a translation mechanism 8 disposed at one side of the rotatable frame supported in an upstanding disposition internally of the detector stand 5 for moving the detectors 3a and 3b in parallel with each other, approaching mechanisms 9a and 9b mounted on the translation mechanism 8, and rotating mechanisms (see FIG. 3) mounted on the approaching mechanisms 9a and 9b, respectively.

The rotatable frame 10 serves for supporting rotatably the pair of detectors 3a and 3b. As can be seen in FIG. 3, the rotatable frame 10 is disposed at a position close to the detector stand 5 at a front side thereof and configured in a rectangular shape as viewed from the front side, as can be seen in FIG. 2. The rotatable frame 10 has a center portion supported rotatably by means of a bearing 11 of a large diameter, as shown in FIG. 2, wherein a pulley 12 is mounted on the rotatable frame 10 at a rear end portion, as shown in FIG. 3. A rotatable drive motor 13 is mounted at a bottom portion of the detector stand 5, as shown in FIG. 2. The rotational drive motor 13 has a rotatable shaft 14 to which the pulley 12 mentioned above is operatively coupled by a transmission belt 15. Thus, by driving the motor 13, the rotatable frame 10 can be rotated through cooperation of the belt 15 and the pulley 12. Parenthetically, the rotational drive motor 13 incorporates an absolute encoder for detecting the amount of rotation (or angular distance) of the rotatable frame 10.

Referring to FIG. 3, the translation mechanism 8 is disposed on one side surface of the rotatable frame 10. The translation mechanism 8 is so arranged as to move the pair of detectors 3a and 3b in the directions parallel to each other in a plane extending orthogonally to the longitudinal axis 16 of the object supporting table 1 while interlocking the detectors 3a and 3b with each other. To this end, the translation mechanism 8 includes a traversing base 17 configured substantially in an inverted C-like shape as viewed from the front side, and guide blocks 18 and 19 mounted, respectively, at top and bottom end portions of the traversing base 17 at a rear side thereof, wherein the guide locks 18 and 19 are placed in slideable engagement with guide rails 20 and 21, respectively, which are mounted on the rotatable frame 10 at top and bottom end portions thereof, respectively, as is shown in FIG. 2. Disposed in the vicinity of the guide block 18 mentioned above is a feed nut 22 which engages screwwise with a feed screw rod 23 having a rotatable shaft portion operatively coupled to a rotatable shaft of a traverse drive motor 24 by means of a belt 25 spanned therebetween. Thus, by driving the traverse drive motor 24, the traversing base 17 can move transversely relative to the rotatable frame 10 in parallel therewith through cooperation of the transmission belt 25 and the feed screw rod nut assembly. Parenthetically, the traverse drive motor 24 incorporates an absolute encoder for detecting the amount of the transversal movement or displacement of the traversing base 17.

As is shown in FIG. 3, the traversing base 17 constituting a part of the translation mechanism 8 is equipped with the approaching mechanisms 9a and 9b. These approaching mechanisms 9a and 9b are so arranged as to move the associated detectors 3a and 3b in the direction approaching toward the object supporting table 1 orthogonally to the direction in which the detectors 3a and 3b are moved by means of the translation mechanism 8 in parallel with each other. To this end, the approaching mechanisms 9a and 9b are comprised of approaching bases 26a and 26b, respectively, each of which is formed substantially in an inverted T-like shape (convex shape), as viewed from the front side in FIG. 2, guide blocks 27 mounted at left and right end portions of the approaching bases 26a and 26b at their rear sides, respectively, and frontwardly projecting guide rails 28 mounted, respectively, at left and right end portions of the traversing base 17 at the front side thereof, as can be seen from FIG. 3. Thus, the approaching bases 26a and 26b can be slidably moved owing to sliding engagement between the guide rails 28 and the guide blocks 27, respectively. Further, as can be seen in FIG. 2, the approaching bases 26a and 26b are equipped with feed nuts 29a and 29b at their ends, respectively, at the rear side, wherein the feed nuts 29a and 29b engage screwwise with feed screw rods 30a and 30b, respectively, and rotatable shaft portions of the feed screw rods 30a and 30b are operatively coupled to rotatable shafts of approaching drive motors 31a and 31b by means of transmission belts 32a and 32b, respectively. Thus, by driving the approaching drive motors 31a and 31b, the approaching bases 26a and 26b are, respectively, caused to move in the direction approaching toward the object supporting table 1 via the belts 32a and 32b and the feed screw rods 30a and 30b. Incidentally, it should be added that the each of the approaching drive motors 31a and 31b incorporates therein an absolute encoder so as to detect the amount of displacement of each of the approaching bases 26a and 26b (i.e., the distance for which the approaching base 26a, 26b has been moved).

Referring to FIG. 2, the approaching bases 26a and 26b of the approaching mechanisms 9a and 9b are provided with rotating mechanisms 33a and 33b, respectively. The rotating mechanisms 33a and 33b serve for rotating the detectors 3a and 3b around the axes thereof, respectively, in a plane extending orthogonally to the longitudinal direction of the object supporting table 1 at the positions of the detectors 3a and 3b after having been moved by the approaching mechanisms 9a and 9b, respectively. To this end, rotatable shafts 34a and 34b which are rotatable around respective axes are provided so as to extend through the approaching bases 26a and 26b at their center portions, respectively, and supported rotatably by means of bearings 35a and 35b, wherein driving motors 36a and 36b for rotating the detectors 3a and 3b are installed internally of the approaching bases 26a and 26b, respectively, as shown in FIG. 3. More specifically, driving gears 37a and 37b mounted on the output shafts of the driving motors 36a and 36b mesh with gears 38a and 38b mounted on one end portions of the rotatable shafts 34a and 34b, respectively. Thus, by driving the driving motors 36a and 36b, the rotatable shafts 34a and 34b are rotated by way of combinations of the driving gears 37a and 37b and the gears 38a and 38b which are associated with the rotatable shafts 34a and 34b, respectively. Each of the driving motors 36a and 36b incorporates an absolute encoder for detecting the rotation or angular displacement of each of the detectors 3a and 3b.

In the structure described above, the detectors 3a and 3b are fixedly mounted on the rotatable shafts 34a and 34b at the tip ends thereof, respectively, as can be seen in FIGS. 2 and 3. By virtue of the arrangement described above, the detectors 3a and 3b can be set or positioned at any given angle relative to the object 2 under examination resting on the object supporting table 1 with desired distance therefrom and in any desired direction toward the object 2 under examination by driving correspondingly the translation mechanism 8, the approaching mechanisms 9a and 9b and/or the rotating mechanisms 33a and 33b.

A control unit 40 shown in FIG. 3 is in charge of controlling the rotatable frame 10, the translation mechanism 8, the approaching mechanisms 9a and 9b, the rotating mechanisms 33a and 33b and others. To this end, the control unit 40 incorporates internally a CPU (Central Processing Unit), a ROM (Read-Only Memory), a RAM (Random Access Memory) and an input/output interface circuit.

The signals outputted from the absolute encoders provided in association with the various electric motors 13, 24, 31a, 31b, 36a and 36b are inputted to the control unit 40 via the input/output interface circuit so that when operator inputs a command indicating a relative angle to be formed between the detectors 3a and 3b through the computer 50, the moving mechanisms mentioned above are automatically so driven that the angle as designated can be established.

Further, each of the detectors 3a and 3b is equipped with a contactless distance sensor for measuring distances between the object 2 under examination and the detectors 3a and 3b, respectively, wherein the detection output signals of the sensors are supplied to the control unit 40. By the structure above mentioned, the detectors 3a and 3b are controlled so that they are stopped when they approach a predetermined distance.

Figure 4:
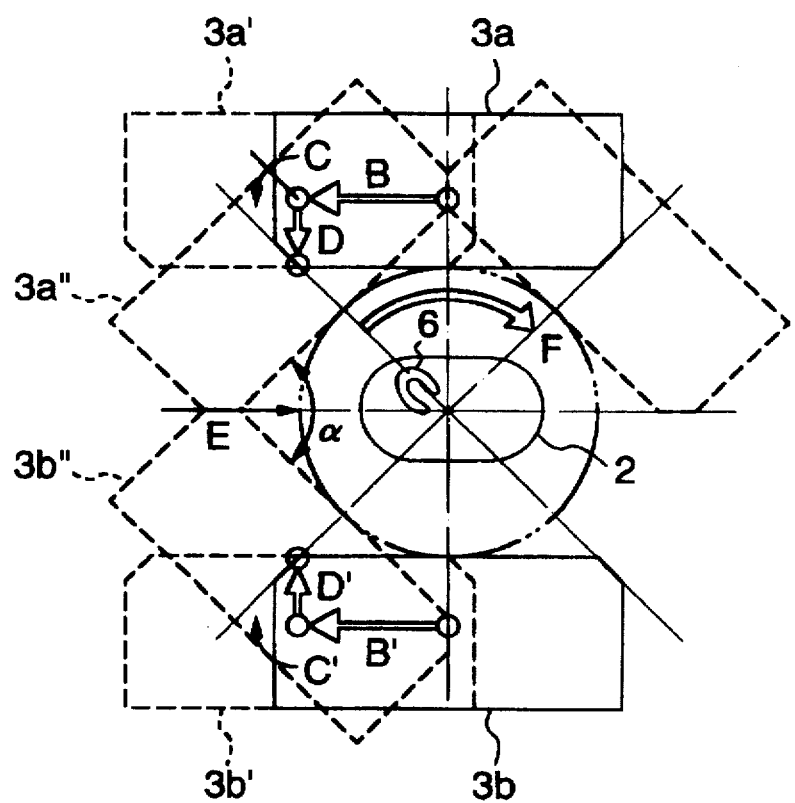
FIG. 4 is a front side view for illustrating schematically movements of the individual detectors in the scintillation camera apparatus according to the invention.

Next, by reference to FIG. 4, description will turn to movements of the paired detectors 3a and 3b in the twin-detector type scintillation camera apparatus implemented in the structure described in the foregoing. FIG. 4 shows schematically and generally a front side view of the scintillation camera apparatus as viewed in the direction toward a head of the object 2 under examination lying on the object supporting table 1 as shown in FIG. 1. It is assumed that the pair of detectors 3a and 3b are disposed above and beneath the object 2 under examination with the latter being interposed therebetween in the initial state. In that case, the heart 6 of the object 2 under examination which is assumed, by way of example, a human being is located at an upper position in a left half of the body of the object 2 under examination relative to the longitudinal axis thereof, as viewed in FIG. 4. Starting from this state, it is attempted to collect data of SPECT images within an angular range of 180 degrees around the object 2 under examination.

In the first place, by driving translation mechanism 8 of FIG. 1, the pair of detectors 3a and 3b are displaced, for example, in the leftward direction as indicated by arrows B and B', respectively, as viewed in FIG. 4. More specifically, the traverse drive motor 24 is driven to draw the feed nut 22 by way of the feed screw rod 23, as viewed in FIG. 2, to thereby move the traversing base 17 leftwardly, whereby the detectors 3a and 3b are moved, as indicated by arrows B and B', respectively, as a result of which the detectors 3a and 3b are displaced to the positions indicated by reference characters 3a' and 3b', respectively, as can be seen in FIG. 4.

Subsequently, the pair of detectors 3a and 3b are rotated on the respective axes, for example, by 45 degrees by driving correspondingly the rotating mechanisms 33a and 33b (see FIG. 2), as indicated in FIG. 4 by arrows C and C', respectively. More specifically, referring to FIG. 3, the driving motors 36a and 36b are driven to thereby rotate the rotatable shaft 34a of one detector 3a counterclockwise by way of the driving gears 37a and 37b while rotating the rotatable shaft 34b of the other detector 3b clockwise via the gears 38a and 38b, respectively. Thus, the upper detector 3a is rotated in the counterclockwise direction with the lower detector 3b being rotated clockwise, as indicated in FIG. 4 by arrows C and C', respectively.

In succession, the pair of detectors 3a and 3b are moved downwardly and upwardly, as indicated by arrows D and D' in FIG. 4, by driving the approaching mechanisms 9a and 9b (see FIG. 1), respectively. More specifically, the upper and lower approaching drive motors 31a and 31b (see FIG. 2) are driven to thereby move away the feed nuts 29a and 29b from each other by means of the feed screw rods 30a and 30b, respectively, whereby the individual detectors 3a and 3b are moved downwardly and upwardly as indicated in FIG. 4 by arrows D and D', respectively, until the detectors 3a and 3b are stopped at respective positions where corner portions of the detectors 3a and 3b are mutually brought into contact in opposition to each other. Thus, the detectors 3a and 3b are displaced to positions indicated in FIG. 4 by 3a" and 3b", respectively, as a result of which the relative angle α between the detectors 3a and 3b is set, for example, at 90 degrees.

Subsequently, in order to move the pair of detectors 3a and 3b from the respective positions 3a" and 3b" closely to the object 2 under examination, the translation mechanism 8 shown in FIG. 1 is actuated to thereby cause the detectors set at the relative angle α of 90 degrees to move rightwardly, as indicated by an arrow E in FIG. 4. In this conjunction, it should be mentioned that in the case where the position at which the detectors 3a and 3b are brought into contact with the object 2 under examination solely by inclining the etectors 3a and 3b is known previously, the detectors 3a and 3b may be moved to the aforementioned position at the initial step, whereupon the detectors 3a and 3b may be revolved to the positions 3a" and 3b", respectively, as shown in FIG. 4.

Thereafter, starting from the state mentioned above, the rotatable frame 10 shown in FIG. 2 may be rotated, for example, in the clockwise direction to thereby cause the paired detectors 3a and 3b at positions 3a" and 3b" to rotate by 90 degrees in the clockwise direction, as indicated by an arrow F in FIG. 4. In more concrete, the rotating motor 13 (see FIG. 2) is driven to thereby rotate clockwise the rotatable frame 10 by means of the belt 15 and the pulley 12. As a result, the paired detectors 3a and 3b set at the relative angle α of 90 degrees are caused to rotate by 90 degrees as a whole with the relative angle α of 90 degrees being maintained as it is. In the course of this rotation, radioactive rays emitted from the object 2 under examination are detected by means of the detectors 3a and 3b. In this way, image data over a range of 180 degrees around the heart 6 of the object 2 under examination can collectively be acquired through cooperation of the pair of detectors 3a and 3b, whereby SPECT images of the heart of the object 2 under examination are made available for the diagnosis purpose.

After acquisition of the SPECT images of a position concerned of the object 2 under examination, the translation mechanism 8, the approaching mechanisms 9a and 9b and the rotating mechanisms 33a and 33b are restored to the original or starting states to thereby move the detectors 3a and 3b away from the object 2 under examination, whereby the initial or starting state illustrated in FIG. 1 is resumed. Thereafter, the image data acquisition processing is executed in a succeeding step. Parenthetically, although it has been described above by reference to FIG. 4 that the relative angle α between the detectors 3a and 3b is set at 90 degrees and that the detectors 3a and 3b are rotated by 90 degrees around the object 2 under examination in the state in which the relative angle α of 180 degrees is maintained, it should be appreciated that the relative angle α may be selected at a given value. Besides, the front faces of the detectors 3a and 3b may be moved toward the object 2 under examination lying on the object supporting table 1 to the position where the front faces of the detectors 3a and 3b are brought into contact with the object 2 under examination. Additionally, the detecting directions of the detectors 3a and 3b may be set in other desired or given direction within a range in which the center axis of the object 2 under examination can thereby be covered.

In order to acquire or collect image data of higher quality of the object 2 under examination, it is preferred to move so closely the detectors 3a and 3b to the object 2 under examination that the front faces thereof are put into contact with a surface of the object 2 under examination, as is illustrated in FIG. 5. In this conjunction, it should easily be appreciated that with the arrangement of the scintillation camera apparatus according to the present invention, such positioning of the detectors 3a and 3b as mentioned above can be realized very easily without any need for moving or positional adjustment of the object supporting table 1 merely by operating or driving appropriately the translation mechanism 8, the approaching mechanisms 9a and 9b and/or the rotating mechanisms 33a and 33b implemented in the arrangement described above. However, in that case, there may arise such situation that an internal organ concerned of the object 2 under examination, e.g. the heart 6, lies outside of the effective visual field (i.e., effective field of view) 39 which is determined by the detecting directions of the detectors 3a and 3b, making it impossible to acquire the desired image data. In order to cope with the problem mentioned above, it is taught according to another aspect of the present invention to rotate the detectors 3a and 3b about the respective axes by driving arbitrarily the rotating mechanisms 33a and 33b for the detectors 3a and 3b, respectively, to thereby set more inwardly the detecting directions of the detectors 3a and 3b, respectively, for changing correspondingly the range of the effective visual field 39' such that the organ concerned, e.g. the heart 6, can fall within the effective visual field 39'. In other words, owing to the teachings of the present invention, those portions of the object 2 under examination which could not be diagnosed with the conventional apparatus known heretofore can be picked up in the form of practically utilizable image data.

Operation such as mentioned above as well as others can automatically be controlled on the basis of commands of the operator as inputted through the control unit 40.

In conjunction with the structure of the scintillation camera apparatus shown in FIG. 1, it has been described that the translation mechanism 8 is so arranged as to move the detectors 3a and 3b in parallel with each other by employing the single traverse drive motor 24 while interlocking the detectors 3a and 3b with each other, it should be understood that the traverse drive motor 24 may be provided in association with each of the detectors 3a and 3b so that the latter can be displaced in dependent of each other.

Many modifications and variations of the present invention are possible in the light of the above techniques. It is therefore to be understood that within the scope of the appended claims, the invention may be practiced otherwise than as specifically described. Further, although the invention has been described in conjunction with diagnosis of the heart of a human being, it goes without saying that the invention can find other applications.

We claim:

1. A twin-detector type scintillation camera apparatus, comprising:

a pair of detectors disposed in opposition to each other with a table for supporting an object under examination being interposed therebetween to detect radioactive rays emitted from said object;

a rotatable frame disposed in a plane extending in a direction orthogonal to a longitudinal axis of said table for supporting said paired detectors at one side thereof;

a translation mechanism mounted on said rotatable frame for moving said detectors in parallel with each other in a plane extending orthogonally to said longitudinal axis of said object supporting table while maintaining parallelism between said detectors;

an approaching mechanism for moving said pair of detectors in directions orthogonal to the directions in which said detectors are moved in parallel with each other by said translation mechanism; and rotating means for driving rotationally each of said detectors, respectively, by a predetermined angular distance from given positions of said detectors, respectively.

2. A twin-detector type scintillation camera apparatus according to claim 1, further comprising:

control means for automatically controlling an angle formed between said detectors and positions thereof in accordance with commands inputted by an operator.

3. A twin-detector type scintillation camera apparatus according to claim 2, wherein said control means includes means for controlling an angle formed between said detectors and positions thereof by detecting at least movement of said rotatable frame, said translation mechanism, said approaching mechanism and said rotating means by sensor means.

4. A twin-detector type scintillation camera apparatus according to claim 1, wherein said translation mechanism includes means for moving said pair of detectors while interlocking said detectors with each other.

5. A twin-detector type scintillation camera apparatus according to claim 1, wherein said translation mechanism includes means for supporting said approaching mechanism and said approaching mechanism includes means for supporting said detectors and said rotating means includes means for revolving said detectors around said means for supporting said detectors.

* * * * *